United States Patent [19]
Renfrew et al.

[11] Patent Number: 5,786,142
[45] Date of Patent: Jul. 28, 1998

[54] ELECTROPHORESIS AND FLUORESCENCE DETECTION METHOD

[75] Inventors: John A. Renfrew, Burlington; James W. Cassidy, Waterloo, both of Canada

[73] Assignee: Visible Genetics Inc., Toronto, Canada

[21] Appl. No.: 452,719

[22] Filed: May 30, 1995

[51] Int. Cl.$^6$ .............................. C12Q 1/68; C25B 1/00; B01D 61/42; G01N 15/06
[52] U.S. Cl. .................. 435/6; 204/182.8; 204/299 R; 364/413.01; 422/68.1; 435/912
[58] Field of Search ...................... 204/299 R, 182.8; 435/6, 91.2; 364/413.01; 422/68.1

[56] References Cited

U.S. PATENT DOCUMENTS

| | | | |
|---|---|---|---|
| 3,742,202 | 6/1973 | Spreitzhofer | 235/183 |
| 4,811,218 | 3/1989 | Hunkapiller et al. | 364/413.01 |
| 5,190,632 | 3/1993 | Fujimiya et al. | 204/299 R |
| 5,354,656 | 10/1994 | Sorge et al. | 435/6 |
| 5,410,412 | 4/1995 | Gombocz et al. | 356/417 |
| 5,419,825 | 5/1995 | Fujii | 204/299 R |

OTHER PUBLICATIONS

Mayrand et al, "The use of fluroescence detection and internal lane standards to size PCR products automatically", App. Theor. Electrophor. 3(1):1–11, 1992.

Swerdlow et al, "Reloading and stability of polyacrylamide slab gels for automated DNA sequencing", Biotechniques 16(4):684–693, 1994.

*Primary Examiner*—W. Gary Jones
*Assistant Examiner*—Jeffrey Fredman
*Attorney, Agent, or Firm*—Oppedahl & Larson

[57] ABSTRACT

An improved electrophoresis and fluorescence detection method for nucleotide sequences comprises a fluorescence sensing region along the path of nucleotide detection, coupled with amplification and integration in an integrator of output signals in the form of activity peaks. The output signal, which is converted to a voltage signal, is summed with a programmable offset generated by an inexpensive eight-bit D/A converter. The offset signal is selected to establish a lower starting point for the dynamic range of analog-digital conversion, and is selected to null some or all of the background fluorescence level. The integrator is switchable under program control. The integrator is switched on for long and short integration intervals. The short intervals permit sensing over a dynamic range accommodating very high levels of fluorescence; very high peaks may be measured and features of the peaks distinguished. The long intervals permit sensing over a dynamic range that is optimized for the peaks associated with the smaller peaks of individual nucleotides. In this way, the dynamic range of the analog-digital conversion permits the highest possible resolution over the range of interest during the time in which the sequencing of the nucleotides takes place. The method of nucleotide sequencing and analysis is fast, economical, and yields data with high resolution.

4 Claims, 7 Drawing Sheets

ELECTROPHORESIS AND FLUORESCENCE DETECTION METHOD

SPECIFICATION

The invention relates generally to apparatus for electrophoretic separation of substances of interest, and fluorescent detection thereof, and relates particularly to separation of sequences of nucleotides and the efficient analysis of data resulting from the detection.

BACKGROUND OF THE INVENTION

While the sequencing of genetic matter is commonly performed at the present time, such sequencing takes a long time and requires expensive equipment. Much attention has been paid in recent years to the goal of making the sequencing happen faster, and in reducing the size and cost of the sequencing apparatus. Despite all of this attention, however, sequencing still takes too long and is too expensive for its full promise to be delivered.

A typical prior art sequencer has a rectangular plate containing an electrophoretic medium. The plate is subject to a strong electrical potential giving rise to a potential gradient running along one dimension of the plate; this dimension of the plate is typically oriented vertically. The genetic material being sequenced is amplified with PCR and consists of fragments of various lengths. Each fragment is tagged with a fluorescent tag. The fragments are electrophoretically separated, and pass through a sensing region. The sensing region is illuminated with light selected to stimulate the tags and a light sensor (typically a photomultiplier tube) is optically coupled with the sensing region. The output of the light sensor may be plotted directly on an electromechanical plotter, or may be converted by signal processing apparatus including an analog-to-digital converter (A/D) for subsequent analysis. The dynamic range of the signal processing apparatus must, of course, be wide enough to accommodate the varying output of the light sensor. However, the resolution of the A/D is dispersed over this range; commonly available A/Ds have resolutions of 8, 12, and 16 bits, with the cost rising dramatically with the number of bits of resolution.

The time interval required to sample and convert a particular analog level is important because it limits how quickly the sequencing can be done, yet the cost of a fast A/D goes up quickly as a function of the number of bits of resolution.

The electrical signals from the light sensor vary over some range. The range includes a very high peak at or near the beginning of a particular sequencing task, and hundreds of much smaller peaks during the data-gathering portion of the task, each smaller peak corresponding to a fragment of some particular nucleotide length. The peaks occur relative to a baseline or background level of signal from the light sensor. In prior-art sequencers of the type that perform an A/D conversion, it is commonplace to establish the gains and offsets such that the A/D converter is able to detect the dynamic range running from a low light level up to a highest sensed level higher than that of the smaller peaks. Such an arrangement has the drawback that the smallest change of analog signal that may be detected by the A/D is not as small as might be preferred, and the highest sensed level is nowhere near as high as the highest levels that may occur, for example during the large peak that often comes at the beginning of the task. That peak is clipped to a level corresponding to the highest sensed level.

One approach to remedy these drawbacks is to select an A/D with much higher resolution, and to set the gain such that the highest level sensed is comparable to the height of the large peak. Such an approach is very expensive since A/Ds with such resolution are very expensive. What's more, since the settling and sampling time go up with the resolution (if price is held constant); maintaining a particular A/D speed with an increase of the resolution makes the cost increase greatly.

It is thus desirable to have a way to increase the effective dynamic range of the signal processing circuitry of the sequencer while using relatively inexpensive and fast lower-resolution A/Ds. It is particularly desirable to increase the effective dynamic range to accommodate peaks that are much higher than the usual nucleotide peaks.

Yet another drawback of present-day sequencers is that it is necessary to establish a timing relationship between the data streams from analysis tracks associated with the various nucleotides (e.g., G, T, A, and C). The timing relationship is typically established relative to the start of a sequencing task and proceeds in a free-running way as the mixture being analyzed is drawn down the column. It would be desirable to have a way to introduce at least one additional known or fixed event permitting a higher-confidence timing relationship between columns and permitting a higher-confidence nucleotide count within a single column.

SUMMARY OF THE INVENTION

An improved electrophoresis and fluorescence detection apparatus has a light sensor juxtaposed with a sensing region. The output signal from the light sensor is a current signal, and the current signal is converted to a voltage signal. The voltage signal is summed with a programmable offset generated by an inexpensive eight-bit D/A converter. The offset signal is selected to establish a lower starting point for the dynamic range of the A/D conversion, and is selected to null some or all of the background light level. The summed signal is amplified and integrated in an integrator. The integrator is switchable under program control. The integrator is switched on for long and short intervals. The short intervals permit sensing over a dynamic range accommodating very high levels of fluorescence; very high peaks may be measured and features of the peaks distinguished. The long intervals permit sensing over a dynamic range that is optimized for the peaks associated with the smaller peaks of individual nucleotides. In this way, the dynamic range of the A/D convertor is set to permit the highest possible resolution over the range of interest during the time in which the sequencing of the nucleotides takes place. The sequencer is fast and economical and yields data with high resolution.

DESCRIPTION OF THE DRAWING

The invention will be described with respect to a drawing in several figures, of which.

DETAILED DESCRIPTION

Figure 1:
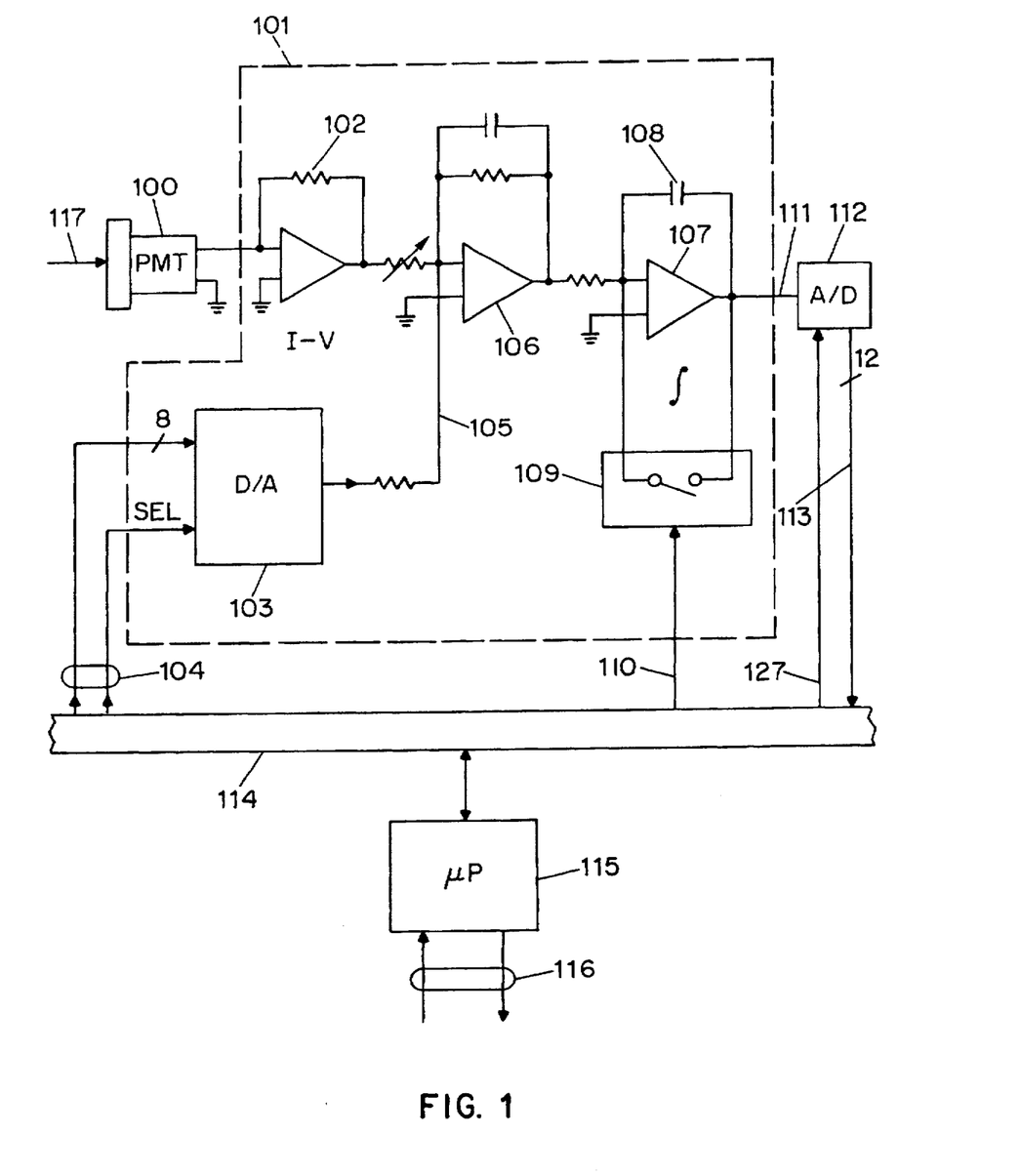
FIG. 1 shows in schematic form a signal processing channel according to the invention.

The invention will first be discussed in connection with FIG. 1, which shows in schematic form an exemplary signal processing channel. Light enters the processing channel via a light path 117, striking light sensor 100, which is preferably a photomultiplier tube (PMT). The PMT has a current output which is related to the incident photon flux. The output of the PMT is converted from a current-level output to a voltage-level output via op amp 102. In a prior art signal processing channel the voltage signal might then be passed directly to an analog-to-digital converter like A/D 112, and the resulting digital signal would be stored for later display and analysis. But in the signal processing channel according to the invention, a DC offset is supplied by circuitry that will now be described. An eight-bit digital-to-analog converter (D/A) 103 is provided, which generates an output on line 105. The output of the D/A is controlled by processor 115 through digital bus 114. Digital bus 114 provides a select line and eight data lines 104 to the D/A 103. In this way, the processor 115 can provide an offset or base level for the signal being processed.

The programmed offset from D/A 103 and the voltage level from amplifier 102 are summed and amplified by op amp 106. The output of op amp 106 is then provided to integrator 107, which comprises an op amp, a highly stable capacitor 108, and related components. Integrator 107 is controllable with respect to the starting and ending time of its integration periods by analog switch 109, controlled by discrete control line 110. The output of the integrator 107 is provided on via line 111 to A/D 112. A/D 112 is preferably a multiple-input A/D, and only one of its inputs is shown in FIG. 1 for clarity. A/D 112 has a serial control line 127 and a serial data line 113, which carries 12 bits of data from the A/D conversion process. Processor 115 has a bidirectional serial link 116 with a personal computer or work station omitted for clarity in FIG. 1.

As will be described in further detail below, in accordance with the invention the dynamic range of the A/D 112 is not spread out over the entire range of possible outputs from the PMT 100. Instead, the offset from D/A 103 is used to set a base level which is the starting point for the dynamic range of the A/D 112. In addition, the integration periods, namely periods during which switch 109 is open so that integration takes place, are sometimes short and sometimes long. Shortening the integration period permits the A/D 112 to extract meaningful data even at times when the photon flux along path 117 is very high, much higher than the flux during times when a tagged nucleotide is present in the sensing area.

Figure 2:
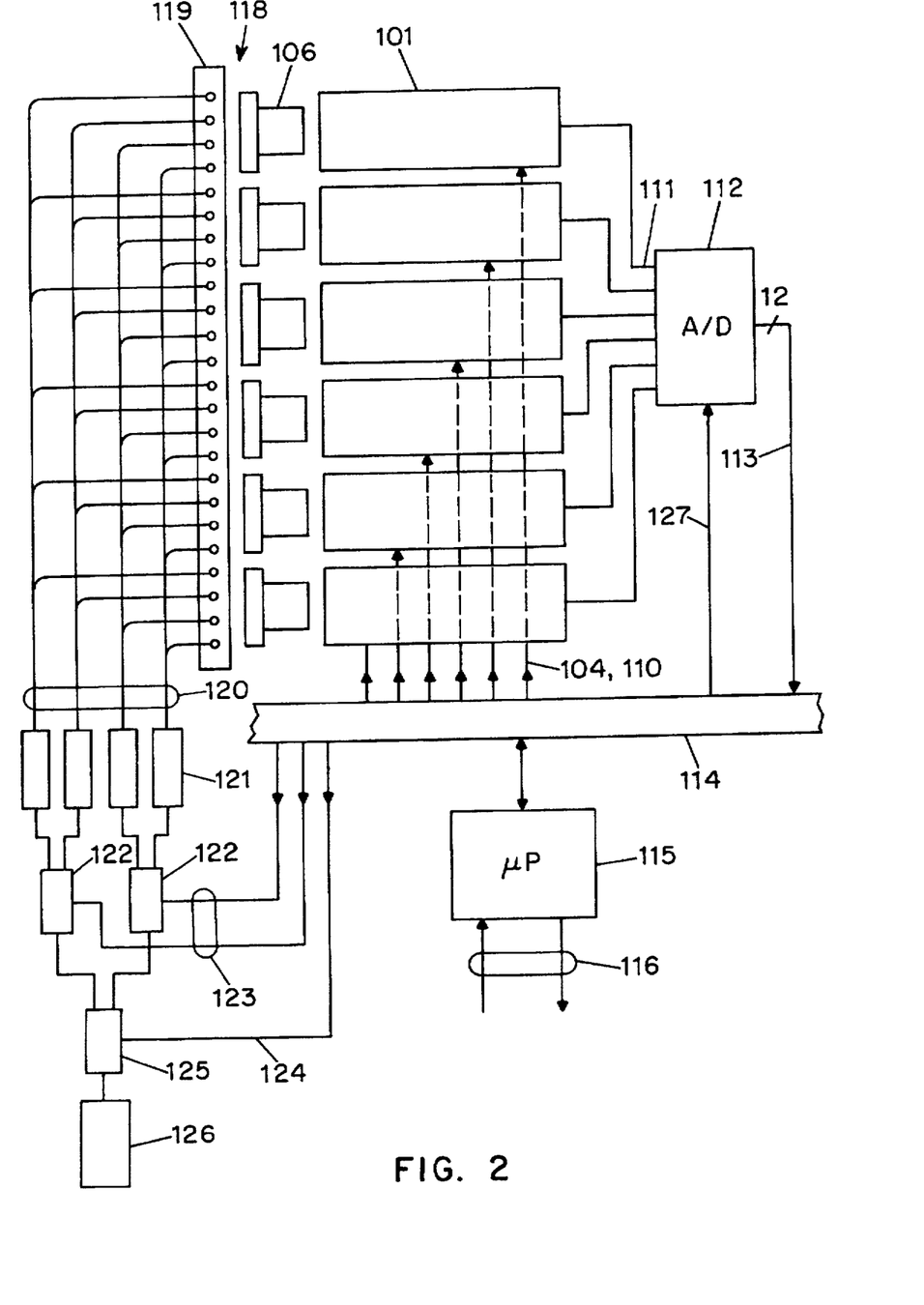
FIG. 2 shows in schematic form an exemplary sequencing apparatus employing signal processing channels according to the invention.

FIG. 2 shows in schematic form an exemplary sequencing apparatus employing signal processing channels according to the invention. The apparatus desirably has as many as twenty-four sensing regions along electrophoresis sensing area 118. The sensing regions are illuminated by light fibers 120 in a manner discussed in some detail below. The light fibers are illuminated by laser 126. The fluorescent activity in the sensing regions is sensed by PMTs 100 as shown. Each PMT has its output processed by signal processing channel 101, controlled by lines 104, 110. The outputs from the channels 101 are provided to multiple-input A/D 112, which has control input 127 and output line 113.

It should be understood that while the term "light" has been used herein, this should not be construed narrowly to visible light but should also be construed to include infrared and ultraviolet light, within the collective term "electromagnetic radiation". The light stimulating the detection area may be visible light, or infrared or ultraviolet, and when fluorescence occurs the emitted light may be visible light, or infrared or ultraviolet. Herein the term "light emitter" or "electromagnetic radiation emitter" is meant to refer to the source of stimulating light which stimulates the detection region, in an exemplary embodiment this is light from a laser, directed to the detection region by a light fiber.

Under processor control, optical switches 125, 122 determine which of four splitters 121 will receive light. The sensing regions are disposed in groups of four, each group juxtaposed with one of the PMTs 100. The light fibers 120 are thus illuminated selectively so that of the four sensing regions juxtaposed with one of the PMTs 100, only one will be illuminated. This arrangement is described in greater detail in U.S. appl. no. 08/353,932, filed Dec. 12, 1994, entitled Automated Electrophoresis And Fluorescence Detection Apparatus And Method, assigned to the same assignee as the assignee of the present application, and incorporated herein by reference.

Figure 6:
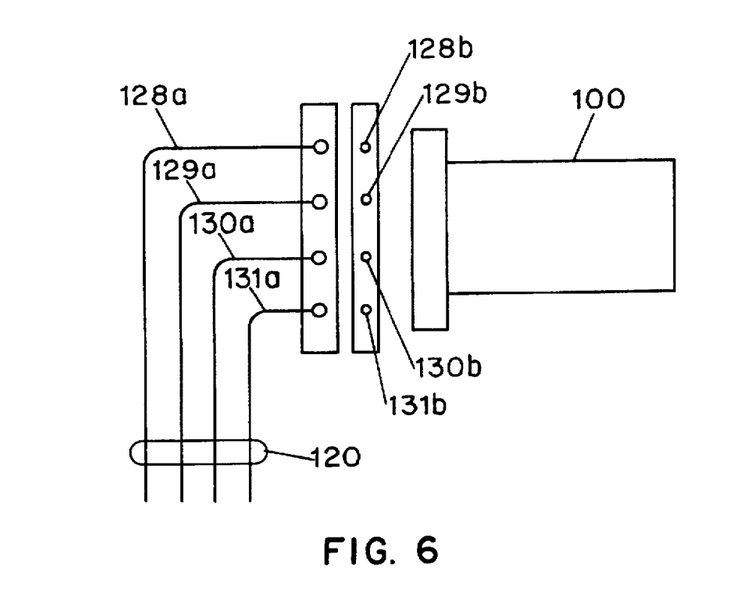
FIG. 6 shows a physical arrangement of four light emitters, four sensing regions, and a photomultiplier tube.

Turning now to FIG. 6, the sensing regions juxtaposed to one of the PMTs 100 are shown in greater detail. Four light emitters 128a, 129a, 130a, and 131a provide light to four sensing regions 128b, 129b, 130b, and 131b. These regions 128b, 129b, 130b, and 131b are preferably disposed within an electrophoresis gel plate, the remainder of which is omitted for clarity in FIG. 6. The PMT 100 is positioned so that it can receive photons from any of the four regions 128b, 129b, 130b, and 131b. It will be appreciated that depending on the design of the PMT, the sensing regions 128b, 129b, 130b, and 131b might have to be closer together in FIG. 6 so that the photons from outlying regions 128b and 131b reach the optically active area in the PMT. Alternatively, focusing lenses omitted for clarity in FIG. 6 can provide optical coupling of each sensing region to the PMT.

Figure 3:
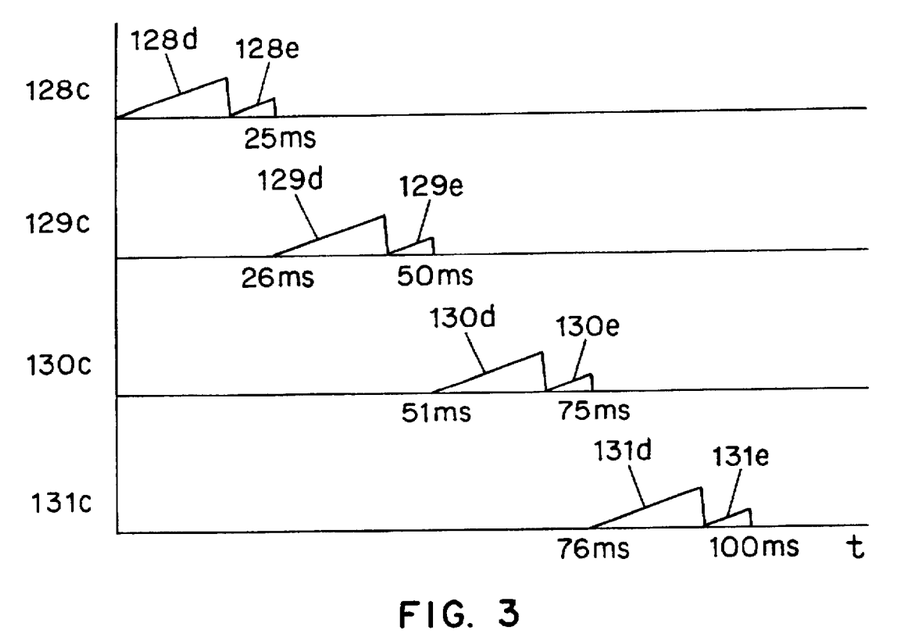
FIG. 3 shows long and short integration intervals or periods based on excitation of four sensing regions.

Returning now to FIG. 3, what are shown are long and short integration intervals or periods based on excitation of four sensing regions for a particular PMT 100. For example, line 128c shows a long integration period 128d associated with the time in which the light fiber 128a is illuminated. What comes next is a short integration period 128e, also associated with the time in which the light fiber 128a is illuminated. (The integration periods are started and stopped under processor control via switches 109, shown in FIG. 1.) Next the switches 125, 122 (FIG. 2) are reconfigured so that light comes from fiber 129a. At about the same time, as shown by line 129c (FIG. 3) a long integration period 129d takes place, followed by a short integration period. The process is repeated for the third and fourth sensing areas 130b and 131b. The eight integration periods, four long and four short, take up one-tenth of a second in total. In this way, nucleotides could arrive at the sensing regions 128b, 129b, 130b, and 131b as frequently as about once per second and would not get missed even though at any particular instant, three of the four channels are not illuminated and thus are not generating any data for analysis.

Figure 4:
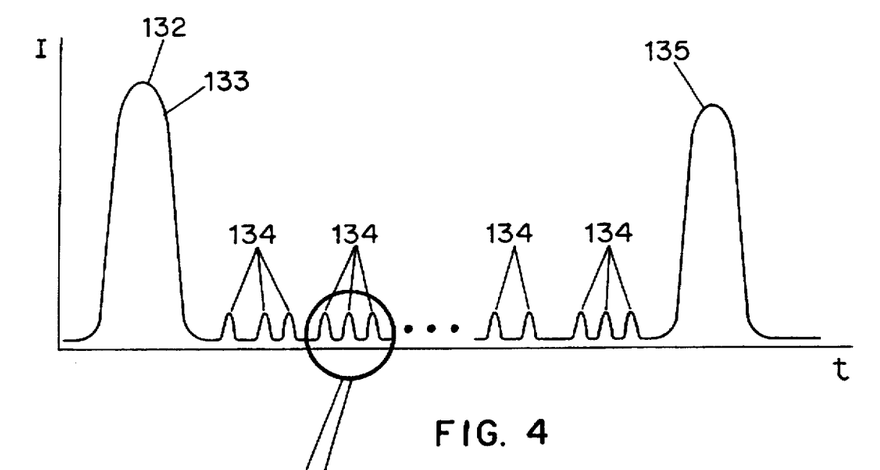
FIG. 4 plots light output as a function of time for a typical sensing region.

FIG. 4, a chromatogram, plots light output as a function of time for a typical sensing region 128b. The PMT output is very high when the sequencing is started, as shown by peak 132. Following this are several dozen or more small peaks 134, each associated with the arrival of a tagged nucleotide at the sensing region 128b. Optionally, as described in detail below, there may come another large peak 135 associated with a buffer additive corresponding to some predetermined number of base pairs, such as 250, 300, or 350 base pairs. It is commonplace to use the large peak 132 as a calibration point that defines the start of the sequencing. In accordance with the invention the second large peak 135 can also be used as a calibration point.

Figure 5:
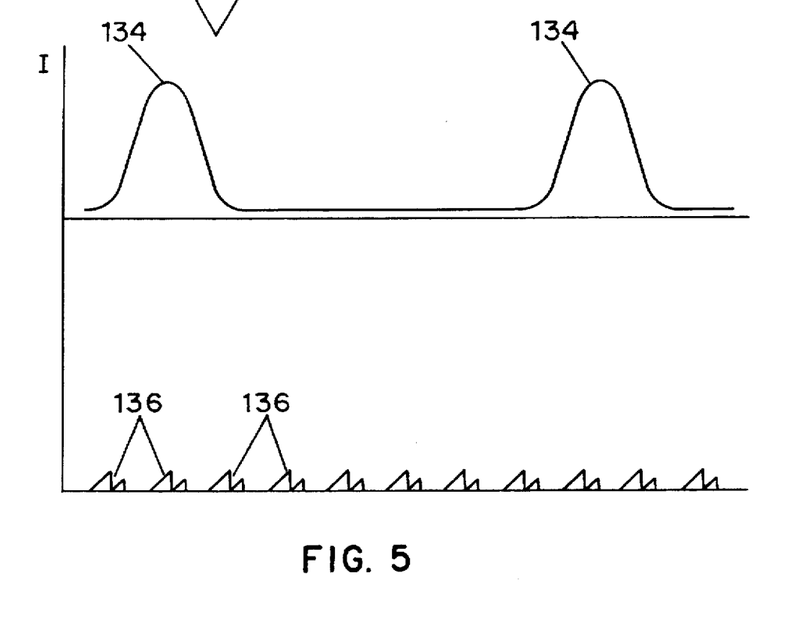
FIG. 5 plots a detail of FIG. 4 and shows long and short integration intervals associated therewith.

FIG. 5 plots a detail of FIG. 4, to give an impression of the approximate time scale for the integration intervals and the time spacing of the peaks associated with the arrival of tagged nucleotides. As an example, two of the peaks 134 are shown. The integration periods 136, also called sampling periods, occur more frequently than the peaks 134. Those skilled in the art will appreciate that this must be so, otherwise a peak 134 might go undetected if it were to fall between sampling intervals 136. In an exemplary embodiment the ratio is about ten to one; ten samplings occur in the time between two adjacent peaks 134.

Figure 7:
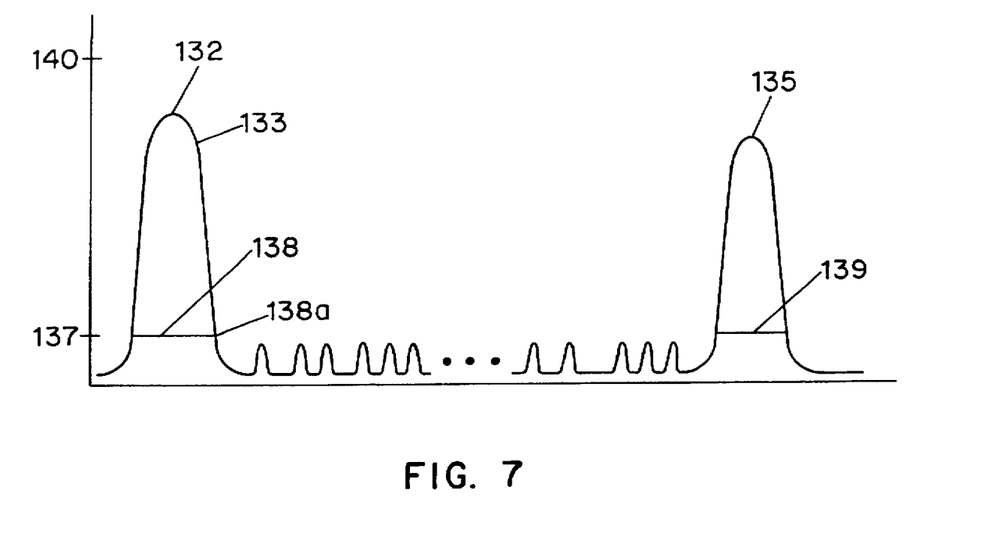
FIG. 7 shows the light output plot of FIG. 4, but with a clipping level.

Turning now to FIG. 7, and with reference to the previously discussed FIG. 4, the tall peaks 132, 135 are shown. Superimposed on the tall peaks 132, 135 are lines 138, 139 which represents the maximum signal capable of being processed by a prior art signal processing channel. The highest output capable of being converted by the A/D converter in such a prior art system is associated with a light level 137. Such a prior art signal processing arrangement has the drawback that the detailed shape of the peak 132 is not available to software for analysis. For example, a trailing edge feature 133 would not be distinguishable from any of the times immediately before and after, since the output from the A/D would simply be the clipped signal 138. The only detectable event associated with the end of the large peak 132 is its intersection with the clipping line 138, at point 138a. For similar reasons no feature of the second large peak 135 is detectable other than the start and end of the clipping line 139.

The tall peaks 132, 135 provide calibration peaks as is well known in the art. The system according to the invention, however, permits meaningful differentiation between small peaks 134 and tall peaks, and permits detection of features of interest in the tall peaks. One way to create tall peaks including peak 135 is to add to the molecules being separated, prior their separation, a substance that yields tall peaks (e.g., a labeled nucleotide of the desired length). A suitable substance that yields tall peaks is a "loading" solution. An exemplary loading solution for use in thin gel DNA electrophoresis, as disclosed in the above-referenced US Appl. No. US 08/353,932, is a solution of 5 mg/ml dextran sulfate blue in 100 % deionized formamide in combination with a solution of fluorophore-labeled DNA fragments of the desired length (i.e., 350 nt) (available from Pharmacia Biotech, Piscataway, NJ) with a final concentration of said fluorophore label of 10 fmol/microlitre. One microliter of loading solution is added to two microliters of a sequencing reaction performed according to the instructions of an AutoRead(tm) 1000 Sequencing Kit (Pharmacia Biotech, Piscataway, NJ). The final 3 microliter volume is loaded into the electrophoresis gel.

One of the advantages of the system according to the invention may now be more fully appreciated with respect to FIG. 7. During a short sampling period such as period 128e in FIG. 3, the impinging light may be at a level as high as the peak 132 or 135 while still integrating to a level within the dynamic range of the A/D 112. Because short sampling periods are interposed among the longer sampling periods, features of the large peaks 132, 135 may be detected and analyzed. Stated differently, the system according to the invention may alternate between short intervals in which the gain is low (that is, during which bright events 132, 135 may be analyzed within the dynamic range of the A/D 112) and longer intervals during which the gain is high (that is, during which the smaller events 134 may be analyzed).

Figure 9:
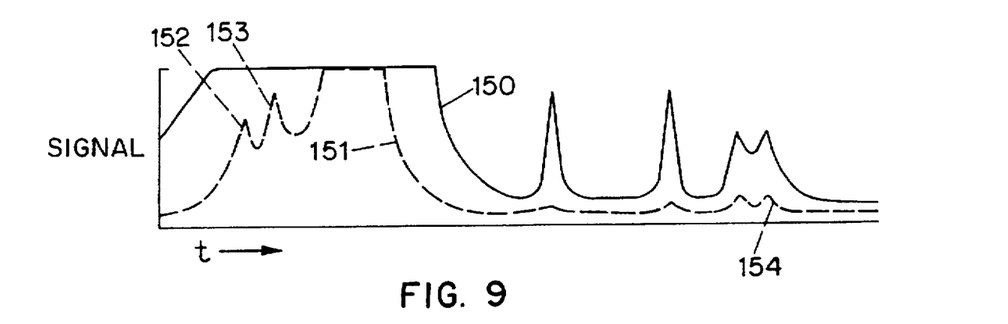
FIG. 9 is a chromatogram showing high-gain and low-gain information juxtaposed.

Signal output from a detection device may optionally be displayed as two separate traces combined in a single chromatogram, as illustrated in FIG. 9. Line 150 represents the trace from the "high gain" intervals, while line 151 represents the trace from the "low gain" interval. The information obtained from the two traces is different, with each trace providing information about the detected molecules not available on the other trace. Peaks labeled 152 and 153 are not identified in line 150. Peak 154, which is difficult to analyze on line 151, shows itself to be in fact two peaks in line 150.

Figure 10:
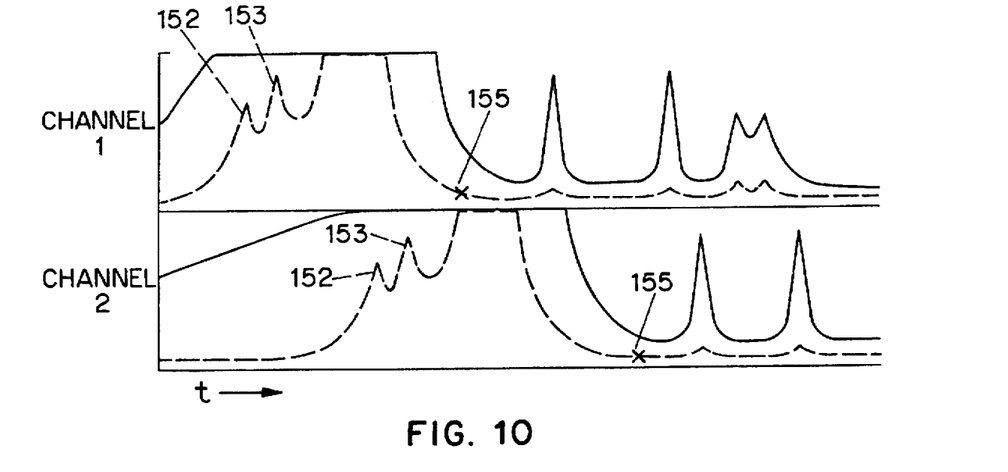
FIG. 10 shows two chromatograms, one for each of two time-skewed channels.
Figure 11:
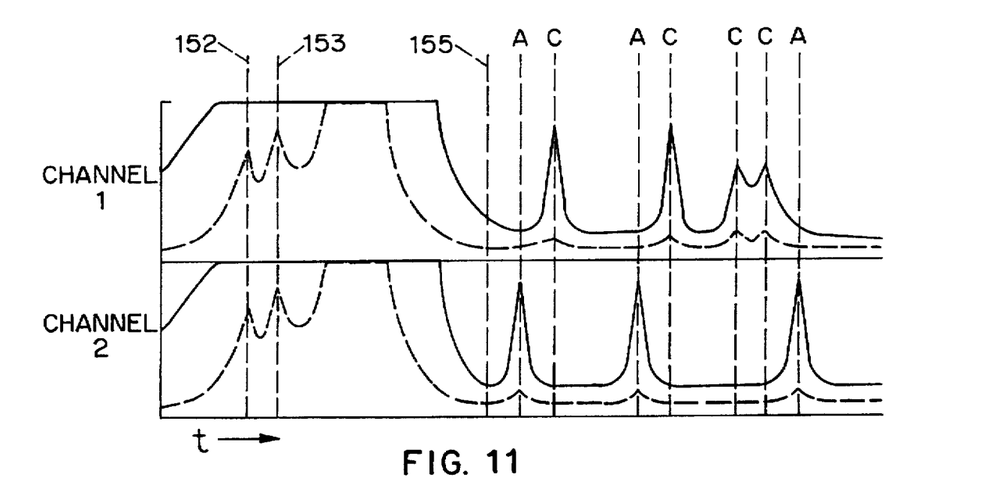
FIG. 11 shows how the availability of high-gain and low-gain information permits establishing a consistent starting time for the two channel chromatograms of FIG. 10.

An advantage of the system according to the invention is illustrated in FIG. 10. In DNA sequencing electrophoresis, chromatograms from four different signal channels, one for A, C, G and T are required. Inconsistencies caused by temperature differences across the gel, separation matrix anomalies, loading well shapes, etc., may lead to misalignment in time between chromatograms. Since it is essential to align the chromatograms in order to determine the relative order of nucleotide bases, misalignment must be corrected. FIG. 10 demonstrates how two channels may be aligned. The tall peaks are consistent from channel to channel, whereas the small peaks vary in relative order. Identification of corresponding tall peak features, such as peaks 152 and 153, and the base of slope 155, allows chromatograms to be synchronized for analysis. FIG. 11 shows aligned signals which permit the relative ordering of the small peaks in the two channels (here representing the A lane and the C lane). A combination of the four channels is then possible (not shown).

Those skilled in the art will appreciate that while the exemplary embodiment has alternating short and long sampling intervals and thus a 1:1 ratio of the number of short and long intervals, the ratio of short to long intervals may just as well be different and nonetheless enjoy the above-described advantage.

In an exemplary embodiment the ratio of the length of the short intervals to the length of the long intervals is one to ten. The two intervals combined add up to about 25 milliseconds. Those skilled in the art will appreciate, however, that the ratio need not be ten to one, and need not necessarily be fixed during a particular sequencing run. The ratio could be greater than four to one or greater than three to one.

Figure 8:
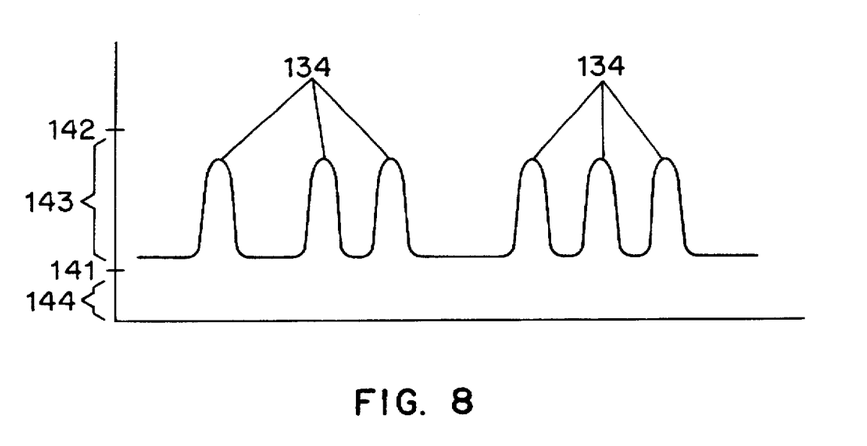
FIG. 8 shows a detail of the light output plot of FIG. 4 with a baseline offset defined.

Another advantage of the system according to the invention may be described with respect to FIG. 8. FIG. 8 shows a detail of the light output plot of FIG. 4. The peaks 134 are shown, which are indicative of tagged nucleotides passing through a sensing region. Experience shows that the range of light output from the PMT tends to fall within some range shown as levels 141 and 142. Ideally the dynamic range of the A/D would be slightly larger than this range, so that the 12-bit resolution gives rise to the ability to detect, say, one four-thousandth of the range 143. This permits sophisticated analysis in software of the signal from the A/D 112.

Two parameters, both controllable in software, permit just this advantageous result, a result not available in some prior art sequencers. First, as mentioned above, the duration of the long sampling intervals may be optimized so that the clipping level of the A/D is only slightly above the peak level 142. Second, under software control the D/A converter 103 may be used to set up an offset level at about level 141. In this way, the A/D converter 112 does not start its dynamic range at zero or at any other arbitrary level that is below the level of interest. Instead, it starts its dynamic range at level 141, so that nearly the entire range of the A/D converter is available for a high-resolution A/D conversion of the range 143 of interest.

In some prior art sequencers it is commonplace to have the A/D converter of the signal processing channel begin its dynamic range at some arbitrarily defined zero level generally indicative of no light entering the PMT. By comparison, in the system according to the invention the D/A 103 is programmable to define the offset 141. This permits the dynamic range of the A/D to start at a level that is closer to the features of interest, for example the valleys between peaks 134. This arrangement offers several benefits, as will be appreciated by those skilled in the art. For example, in the embodiment shown there are six relatively inexpensive D/As 103 and only one relatively expensive A/D 112. Preferably the D/As 103 are of coarser resolution, for example 8-bit, by comparison with the resolution of the A/D 112. The reason for this is simple -- most of the signal processing downstream of A/D 112 relates to the relative heights of the peaks 134 as compared to each other, and the absolute levels of the heights are generally of little interest. In this embodiment the number of D/As 103 corresponds to the number of PMTs, so that if there are any systematic differences in the performance of the PMTs giving rise to differentials between one PMT and the next, the D/As may be programmed to minimize the results of the differentials.

Those skilled in the art will also appreciate that experience may show some part of the waveforms to be of more or less interest in sequencing. For example, if experience shows that it is preferable to concentrate attention on the top halves of the peaks 134, then with the apparatus according to the invention it is a straightforward matter to program the D/As 103 to start the dynamic range of the A/D at some point within the range 143 (FIG. 8).

In the way set forth above, it is possible to control in software the lowest and highest parts of the dynamic range of the A/D. The lowest part is set by the D/A 103, while the highest part is set by the gain, which is determined as a result of the integration interval due to opening and closing of the switch 109. This control is available in real time, and permits interleaving of high-gain and low-gain data collection during an electrophoretic analysis. Those skilled in the art will appreciate that while this is described in connection with nucleotide sequencing, in fact these benefits obtain when an electrophoretic column with the system according to the invention is used for any fluorescently tagged analysis.

Figure 12:
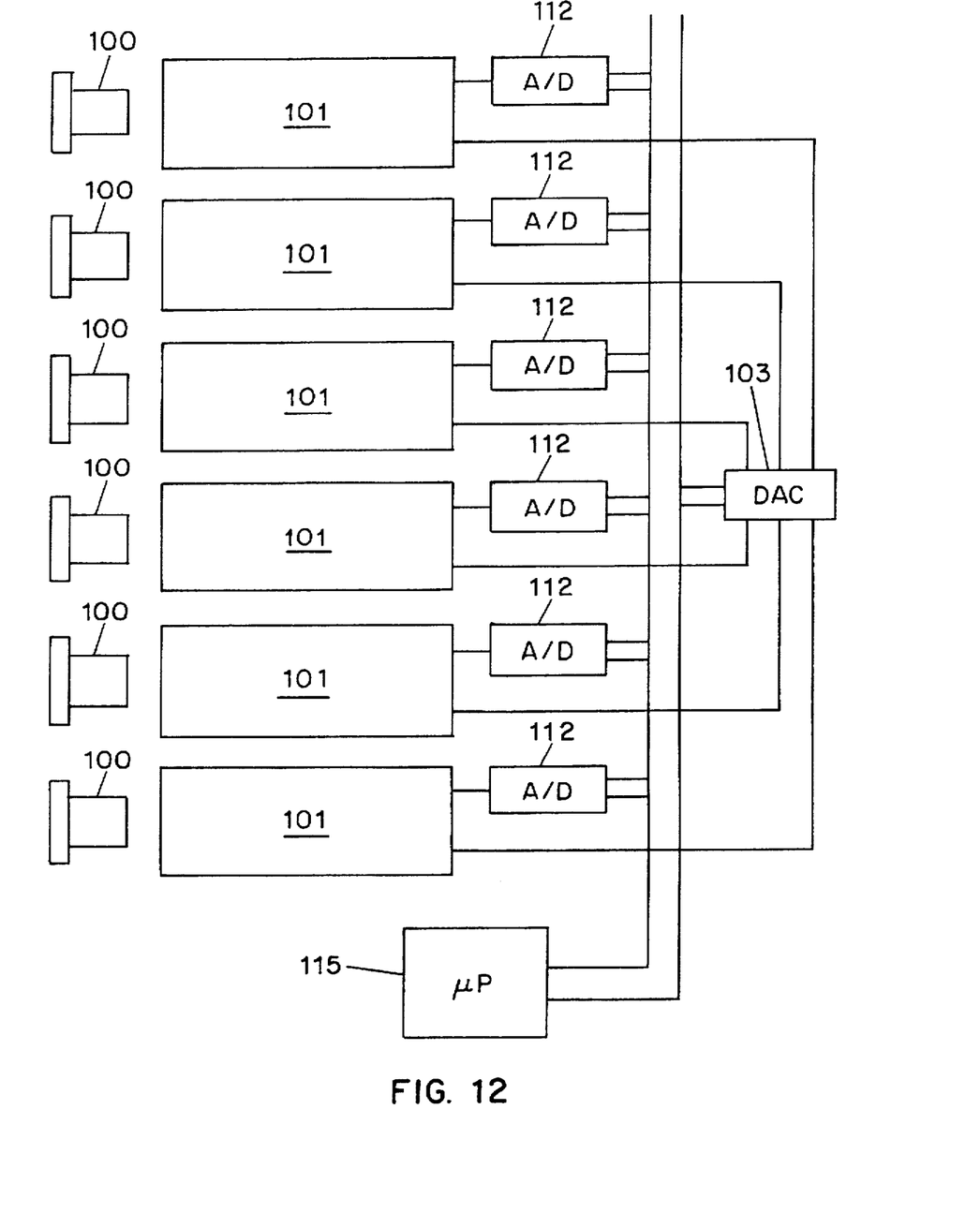
FIG. 12 shows an alternative embodiment of a signal processing system according to the invention.

In an alternative embodiment as shown in FIG. 12, it is possible to employ as many A/D convertors as there are PMTs. This is, of course, more expensive than the multiplexed arrangement of FIG. 2. It offers the prospect of greater sampling rates. In this embodiment the data output from the A/D convertors may be a parallel data bus rather than the serial bus of FIG. 2. This arrangement also employs a single D/A 103 rather than the multiple D/As of FIG. 2. The use of a single D/A is workable because the demands on it are not high. In one protocol the offset is determined only once, at the beginning of the electrophoresis run. Experience may show, however, that it is desirable to have a floating offset, namely, an offset that is readjusted over the course of the run.

What is claimed is:

1. A method of electrophoretic separation of a mixture of fluorescent-tagged nucleotide sequence fragments of varying base pair lengths, the fragments each having fluorescent activity at a first level of photonluflux, the method comprising the steps of:

adding an additive to the mixture, the additive having a fluorescent activity substantially higher than the first level, the additive having a size and charge giving rise to separation corresponding to a predetermined fragment size;

electrophoretically separating the mixture along a path after adding the additive;

stimulating a sensing region within the path; and sensing the combined fluorescent activity of the fragments and of the additive in the sensing region over a dynamic range in an analog-to-digital conversion, said range sufficient to distinguish the activity of the fragments from the activity of the additive, and sufficient to detect features in the activity of the additive at an activity level substantially higher than the first level.

2. The method of claim 1 wherein the sensing further comprises juxtaposing a sensor with the sensing region, the sensor having an electrical output indicative of detected fluorescence; and an integrator responsive to the output, said integrator integrating over repeated short integration intervals and repeated long integration intervals, the short intervals being less than half as long in duration as the long intervals.

3. The method of claim 2 wherein the short integration intervals are less than one-third as long in duration as the long integration intervals.

4. The method of claim 3 wherein the short integration intervals and the long integration intervals alternate.

* * * * *

UNITED STATES PATENT AND TRADEMARK OFFICE
CERTIFICATE OF CORRECTION

PATENT NO    : 5,786,142
DATED        : Jul. 28, 1998
INVENTOR(S)  : Renfrew et al.

It is certified that error appears in the above-identified patent and that said Letters Patent is hereby corrected as shown below:

Column 8, line 21, change "photonluflux" to --photon flux--.

Signed and Sealed this

Sixth Day of October, 1998

Attest:

BRUCE LEHMAN

Attesting Officer

Commissioner of Patents and Trademarks